United States Patent [19]

King

[11] Patent Number: 5,629,471

[45] Date of Patent: May 13, 1997

[54] SAMPLING AND MEASURING DEVICE WITH CALIBRATING PISTON

[75] Inventor: James D. King, San Antonio, Tex.

[73] Assignee: Southwest Research Institute, San Antonio, Tex.

[21] Appl. No.: 621,768

[22] Filed: Mar. 22, 1996

Related U.S. Application Data

[63] Continuation of Ser. No. 310,863, Sep. 22, 1994, abandoned.

[51] Int. Cl.⁶ .................................................. G01N 1/14
[52] U.S. Cl. .................................................. 73/1.01
[58] Field of Search ........................... 73/1 R, 1 G, 4 R, 73/863.84, 864.35, 864.81; 324/308, 317, 321, 202, 228, 601, 663, 672–675

[56] References Cited

U.S. PATENT DOCUMENTS

| | | | |
|---|---|---|---|
| 3,184,973 | 5/1965 | Bradley | 73/422 |
| 3,282,113 | 11/1966 | Sachnik | 73/863.84 |
| 3,726,143 | 4/1973 | Enarsson | 73/422 |
| 4,147,062 | 4/1979 | Jaeger | 73/422 |
| 4,307,620 | 12/1981 | Jiskoot | 73/863.61 |
| 4,390,957 | 6/1983 | Skarlos et al. | 364/550 |
| 4,744,244 | 5/1988 | Tanaka | 73/4 R |
| 4,744,255 | 5/1988 | Jaeger | 73/863.84 |
| 4,820,990 | 4/1989 | Moore | 73/684.35 |
| 4,926,674 | 5/1990 | Fossum et al. | 73/4 R |
| 5,129,267 | 7/1992 | Nicholls | 73/863.84 |

FOREIGN PATENT DOCUMENTS 2097536  11/1982  United Kingdom .................. 324/601

*Primary Examiner*—Robert Raevis
*Attorney, Agent, or Firm*—Baker & Botts, L.L.P.

[57] ABSTRACT

A method and apparatus for sampling and measuring a physical property of a product in a container (11). The container (11) has an aperture (11a) in its bottom surface, to which a sampling tube (13) is affixed. A piston (14) moves back and forth in the sampling tube (13), thereby withdrawing and replacing samples of product via the aperture (11a). While a sample is in the sampling tube (13), a sensor (15) senses a measured value of the physical property of interest. The piston (14) has a calibration layer (14a) that is made from a material having a property that is similar to that of the product with respect to the property of interest. For calibration, the piston (14) is positioned so that the sensor (15) senses a measured value that can be compared to a reference value to determine if the sensor output is properly calibrated.

19 Claims, 2 Drawing Sheets

5,629,471

SAMPLING AND MEASURING DEVICE WITH CALIBRATING PISTON

This application is a continuation of application Ser. No. 08/310,863, filed Sep. 22, 1994, entitled "Sampling and Measuring Device with Calibrating Piston" by James D. King, now abandoned.

TECHNICAL FIELD OF THE INVENTION

This invention relates to an apparatus for obtaining samples of a product from a container and measuring a physical property of interest, and more particularly to an apparatus that uses a non-intrusive sensing device having built-in calibration means.

BACKGROUND OF THE INVENTION

U.S. Pat. No. 5,129,267, entitled "Flow Line Sampler", describes a sampling device for obtaining measurements of product in a flow line. A sample tube is attached to an aperture in the flow line. A piston moves reciprocally within the sampling tube, thereby removing a sample of the product from the flow line and subsequently replacing it. While the sample is in the sample tube, a non-intrusive sensor, such as a nuclear magnetic resonance sensor, measures physical properties of the sample. One feature of the sampling device is that its piston may have a hollow cavity into which a material of known physical properties may be placed, and measured for calibration purposes.

SUMMARY OF THE INVENTION

One aspect of the invention is an apparatus for obtaining a sample of a product from a container having a sampling aperture, and for measuring a physical property of the sample. The product may be any solid, liquid, or gas. A sampling tube is attachable to the container, such that it receives a sample via the sampling aperture. The sampling tube has a port end in communication with the sampling aperture and has a stopper end opposite the port end. A piston is moveable within the sampling tube, and has a substantially sealed relationship with the inner walls of the sampling tube. This permits the piston to be moved upwardly within the sampling tube to provide an upward force at the bottom surface of the sample to return the sample to the container via the sampling aperture. A sensor senses the physical characteristic of the sample while the sample is within the sample tube. For calibration purposes, at least a portion of the piston is made from a calibrating material having a known physical characteristic, such that the sensor output has a known expected value. During calibration, the piston is positioned so that the sensor measures the calibration material and obtains a measured value that can be compared to the expected value.

An advantage of the invention is that it permits a small, relatively inexpensive sensor to be used for automated measurement of any material in any type of container. It eliminates the need for a special sensor configuration for different applications. The result is improved process monitoring and control during any manufacturing process that requires process material having certain physical characteristics.

DETAILED DESCRIPTION OF THE INVENTION

The self-calibrating sampler of the present invention may be used to obtain samples of product in any type of container. It is suitable for use with any solid, liquid, or gaseous product. The container may be an open or closed container or may be a flow line, such as a pipe. The sampler is non-intrusive, requiring only a sampling aperture at the bottom of the container.

Figure 1:
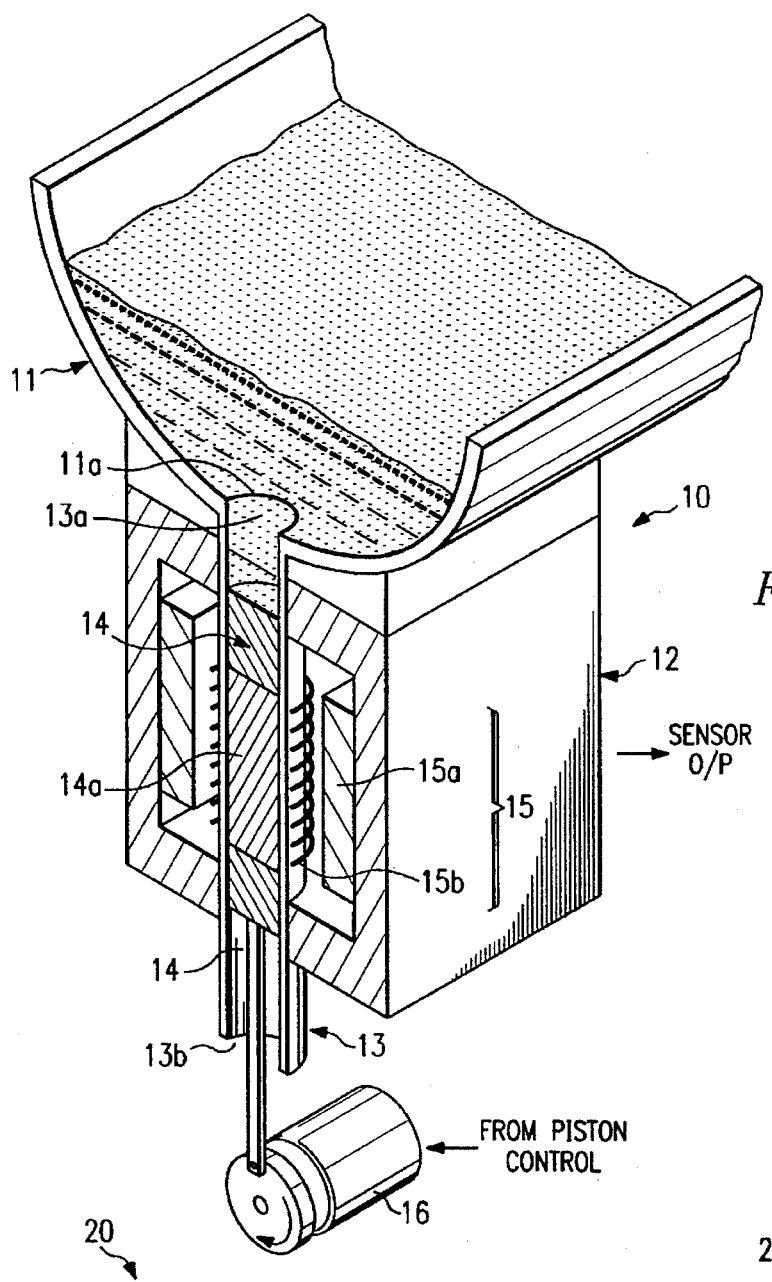
FIG. 1 illustrates a sampling and measuring device having a calibration layer in accordance with the invention.

FIG. 1 is a cross-sectional view of self-calibrating sampler 10. For purposes of example, the container from which product is sampled is an open flow line 11. The housing 12 of sampler 10 is attached to the bottom outer surface of flow line 11. An aperture 11a in the flow line 11 permits product from the flow line to fall, or become sucked into, sample tube 13.

Sample tube 13 has a port end 13a and a stopper end 13b. Port end 13a is connected to flow line 11 around the diameter of aperture 11a to receive product samples from flow line 11. In the preferred embodiment, sample tube 13 mounts orthogonally to the bottom surface of flow line 11. There is a leak proof seal between flow line 11 and sample tube 13 at aperture 11a. Sample tube 13 temporarily stores each product sample that is removed through sampling aperture 11a, while its property of interest is being sensed.

Sample tube 13 and piston 14 provide a means for setting the size of samples. More specifically, sampling tube 13 may be of different sizes and shapes. Also, for a given size of sampling tube 13, the travel of piston 14 may be adjusted so that stopper end 13b is located according to the retracted cycle of piston 14, and different amounts of samples are contained within sampling tube 13.

Sensor 15 has a sensory area that includes some portion of sampling tube 13 between port end 13a and stopper end 13b. Sensor 15 may comprise any sensor capable of measuring a physical property of interest of a sample while the sample is in sampling tube 13. Examples of physical properties that could be measured with an appropriate sensor 15 are: dielectric constant, microwave absorption, electrical resistance, infrared absorption, nuclear magnetic resonance, electric field or magnetic field.

In the example of this description, sensor 15 is a hydrogen transient nuclear magnetic resonance (HTNMR) sensor. Thus, it has a magnet 15a and coil 15b. The property of interest is hydrogen content per unit volume. The output of HTNMR sensor 15 is a voltage that indicates the hydrogen content of the sample being measured.

Piston 14 provides a means for transferring samples from flow line 11 through aperture 11a to sampling tube 13, and for returning samples to flow line 11 through aperture 11a after sensor 15 senses the property of interest. Piston 14 fits snugly within sampling tube 13 and its movement is reciprocating between port end 13a and stopper end 13b.

The movement of piston 14 from port end 13a to stopper end 13b causes product to exit flow line 11 through aperture 11a and to enter sampling tube 13. The forces that cause a product sample to enter sampling tube 13 may be a pressure differential that piston 14 creates by changing position between port end 13a and stopper end 13b, or a gravitational force that the product experiences above aperture 11a, or a combination of these forces.

As piston 14 moves from stopper end 13b to port end 13a, piston 14 exerts positive pressure to cause the sample to exit sampling tube 13 through aperture 11a and return to flow line 11. In one embodiment, piston 14 engages aperture 11a to seal sampling tube 13 from the product in flow line 11 when piston 14 is positioned at port end 13a.

An actuator 16 provides the mechanical movement of piston 14. Various known means, such as a rotating motor, may be used for actuator 16. Further details describing the general structure and operation of a sampling device, but without the calibration features of the present invention, are set out in U.S. Pat. No. 5,129,267, which is incorporated herein by reference.

A feature of sampler 10 is its compact and rugged design, which permits it to be used in extreme environmental conditions. However, a result of such use is that the calibration of the output of sensor 15 may become misadjusted. It is desirable for sampler 10 to have some means for determining the effects, if any, of these environmental conditions on the output of sensor 15.

U.S. Pat. No. 5,129,267 describes one means for calibrating sampler 10. As described therein, piston 14 may have a hollow chamber in which a material having known properties may be placed.

FIG. 1 illustrates an alternative calibration means. In FIG. 1, piston 14 has at least one calibration layer 14a. Layer 14a has known physical characteristics such that it provides an "expected" output of sensor 15.

For example, sensor 15 may be a HTNMR sensor, and the product to be measured may have a hydrogen content (per unit volume) within a certain expected range of values. The material for calibration layer 14a will be selected so that it has a hydrogen content (per unit volume) within that range. Ideally, the T1 and T2 characteristics of the product and the calibration material are also similar. Various polymers with a wide range of hydrogen contents are available or can be fabricated, so as to mimic the product being measured.

Alternatively, sensor 15 might be an NMR sensor that measures a property other than hydrogen content. For example, if the product contained metal, sensor 15 might measure a surface signal. Layer 14a would be made from a similar metal.

As another example, sensor 15 might be a capacitance gauge. In this case, the material for calibration layer 14a would be selected so that its dielectric constant is similar to the expected dielectric constant values of the product being sampled.

Although not shown in FIG. 1, rather than having a layer 14a, piston 14 could be made entirely of a calibration material. In general, the height of the calibration layer 14a relative to the length of piston 14 is not important, except to the extent that, during calibration, the calibration layer 14a must be positionable within the sensory area of sensor 15.

Calibration layer 14a might also be for zero-point calibration, in which case calibration layer 14a would be made from a material designed for a zero reading of sensor 15. For example, calibration layer 14a could be simply a hollow layer filled with air. The material used for calibration layer 14a could depend on the type of sensor 15. For example, if sensor 15 is a NMR sensor, a zero-point reading could be obtained if calibration layer 14a were made from a material not containing hydrogen, such as glass.

Figure 1A:
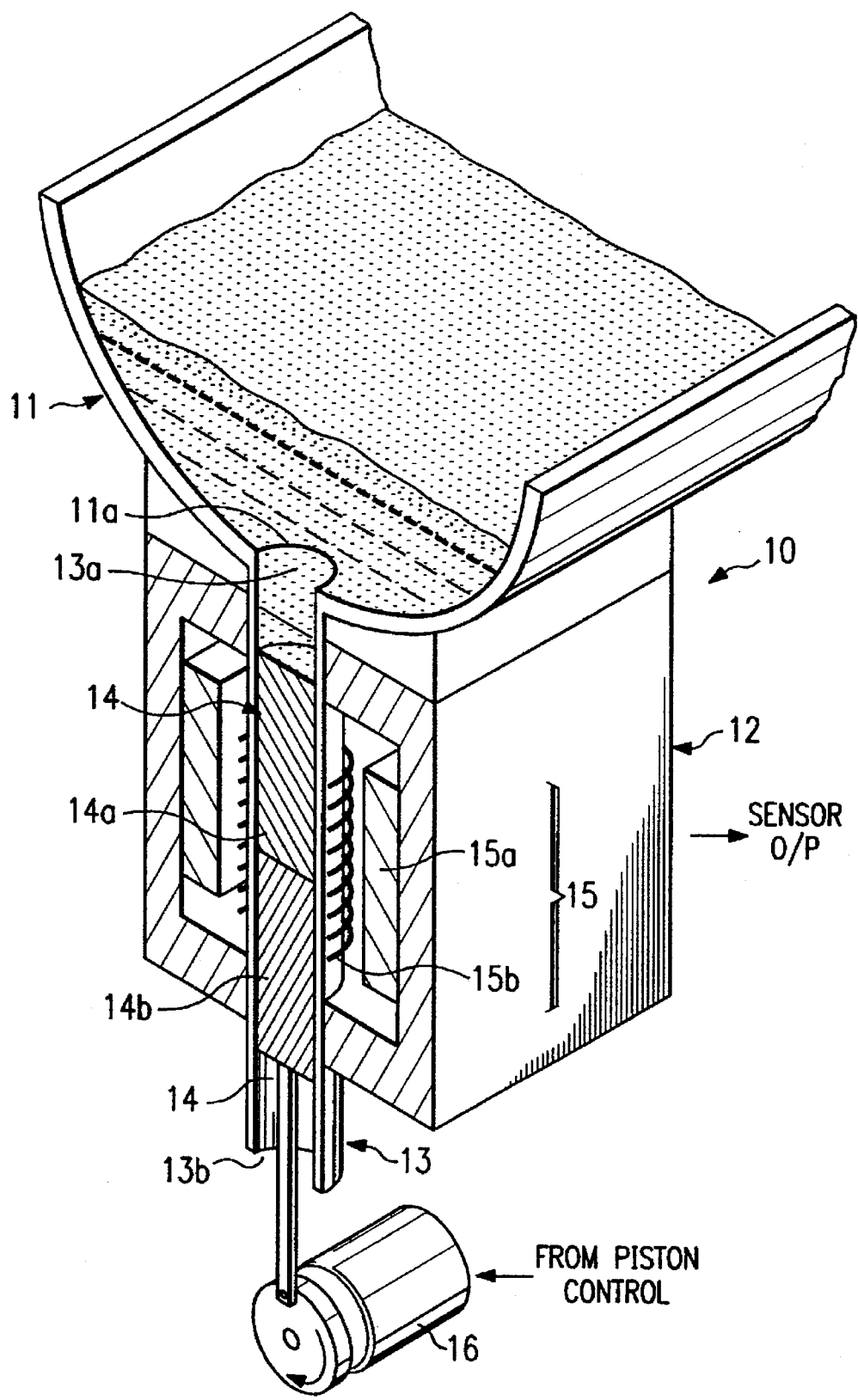
FIG. 1A illustrates a sampling and measuring device having two calibration layers, including a zero-point calibration layer.

FIG. 1A illustrates an embodiment of the invention used for both measurement calibration and zero-point adjustment. A first calibration layer 14a is made from a material whose expected measured value is some known value. A second calibration layer 14b is made from a material whose expected sensor output is zero. Piston 14 is thus suited for both zero-point calibration and calibration at some non-zero value.

Figure 2:
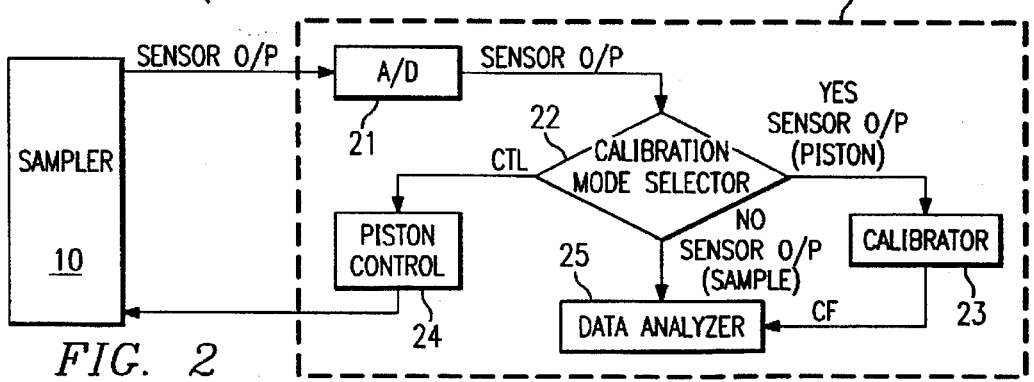
FIG. 2 illustrates an automated sampling and measuring system that uses the device of FIG. 1.

FIG. 2 is a block diagram of a sample-and-measure system 20, which uses the sampler 10 of FIG. 1. The output of sensor 15 is typically an analog signal. For example, where sensor 15 is an HTNMR sensor, its output may be a voltage that indicates a measured number of hydrogen nuclei. The sensor output is converted to a digital signal by an analog-to-digital (A/D) converter 21. A calibration mode selector 22 determines whether the sampler 10 is to be calibrated. Calibration mode selector 22 may be operated by a user who determines that a need for calibration exists. Or, calibration mode selector 22 may be operated automatically, such as in response to environmental conditions or a timing signal.

If sampler 10 is in its calibration mode, a calibrator 23 delivers a signal to piston control unit 24, which causes piston 14 to move to a position inside sampling tube 13, such that the calibration layer 14a is within the sensing area of sensor 15. While piston 14 is in the calibration position, a reading of sensor 15 is taken, for an actual output value, A. This value is compared to a reference (expected) output value, R. The difference value, R−A, is used to derive a calibration factor. Thus, for example, if:

$$R-A=0.1$$

,then the calibration factor (CF) might be calculated as follows:

$$CF = \frac{1}{1-0.1}$$

,and subsequent measurements multiplied by this factor to obtain a correct reading. If there is no difference between the reference value and measured value, the calibration factor is 1.

When sampler 10 is not in the calibration mode, piston control unit 24 causes piston 14 to move up and down so as to obtain one or more samples from container 11. For each sample, sensor 15 obtains a value representing some physical property of interest. The general operation of sampler 10 to obtain samples and measure physical characteristics is described in U.S. Pat. No, 5,129,267, incorporated by reference above. To implement the calibrated output method of this invention, calibrator unit 23 supplies a calibration factor, which is delivered to data analyzer 25. Data analyzer 25 receives output values from sensor 15 and uses the calibration factor to calculate a calibrated output.

The various processing and control units of FIG. 2, specifically, calibration mode selector 22, calibrator 23, piston control unit 24, and data analyzer 25, may be implemented as processes executed by a processor. In fact, as indicated by the dotted lines, all control and process components of system 20 could be implemented by means of a computer system 20a, which has memory for storing instructions for carrying out these processes. Alternately, certain tasks, such as those performed by calibration selector 22, calibrator 23, and piston control unit 24, could be implemented as logic circuits for processing data so as to accomplish the designated tasks. In general, each of the processing and control units of FIG. 2 may be generally regarded as "processors", regardless of whether implemented as software or hardware.

Furthermore, although FIG. 2 includes A/D converter 21, the process illustrated in FIG. 2 could be performed as an analog process, with signal processing techniques being used by calibration mode selector 22, calibrator 23, and piston controller 24. Data analyzer 25 could be as simple as a meter with a means for multiplying the measured signal by the calibration factor during product sampling and measuring.

Other Embodiments

Although the invention has been described with reference to specific embodiments, this description is not meant to be construed in a limiting sense. Various modifications of the disclosed embodiments, as well as alternative embodiments, will be apparent to persons skilled in the art. It is, therefore, contemplated that the appended claims will cover all modifications that fall within the true scope of the invention.

What is claimed is:

1. An apparatus for obtaining a sample of a product from a container having a sampling aperture, and for measuring a physical characteristic of the sample, comprising:

a sampling tube for attachment to said container, such that it receives said sample via said sampling aperture, said sampling tube having a port end in communication with said sampling aperture and having a stopper end opposite said port end;

a piston moveable within said sampling tube, having a substantially sealed relationship with the inner walls of said sampling tube such that said piston may be moved upwardly within said sampling tube to provide an upward force at the bottom surface of said sample to return said sample to said container via said sampling aperture; and a sensor for sensing said physical characteristic of said sample while said sample is within said sample tube;

wherein at least a layer of said piston is made from a calibrating material such that said layer provides a known expected output of said sensor when said layer is positioned within said sample tube within the sensory area of said sensor, and wherein said layer forms an integral body with the rest of said piston;

whereby no piston structure is positioned between the side surface of the layer and sampling tube.

2. The apparatus of claim 1, wherein said sensor is a hydrogen transient nuclear magnetic resonance sensor and wherein said calibrating material has a hydrogen content within the range of the expected hydrogen content of said product.

3. The apparatus of claim 1, wherein said sensor is a capacitance gauge, and wherein said calibrating material has a dielectric constant within the range of the expected dielectric constant of said product.

4. The apparatus of claim 1, wherein said piston is entirely made from said calibrating material.

5. A method of obtaining calibrated measurements of a physical characteristic of a product in a container, comprising the steps of:

selecting a calibration material having at least one physical characteristic that provides an expected sensor output;

placing a sampling tube under an aperture at the bottom of said container, at least part of said sampling tube being within the sensory area of a sensor;

moving a piston inside said sampling tube, said piston having at least a layer made from said calibration material, to a position such that said layer is within the sensory area of said sensor, wherein said layer forms an integral body with the rest of said piston and whereby no piston structure is positioned between the side surface of the layer and sampling tube;

sensing said layer, thereby obtaining a signal representing a measured sensor output of said layer;

comparing the measured sensor output of said layer to said expected sensor output;

determining a calibration factor, using the results of said comparing step;

moving said piston to a position such that said sampling tube receives a sample of said product via said aperture;

sensing said sample, thereby obtaining a signal representing a measured sensor output of said sample; and adjusting said measured sensor output of said sample, using said calibration factor.

6. The method of claim 5, wherein said expected sensor output is zero.

7. The method of claim 5, wherein said expected sensor output is a value determined by a measured physical characteristic of said material similar to a measured physical characteristic of said sample.

8. The method of claim 5, wherein said physical characteristic is hydrogen content, and wherein said sensing steps are performed by sensing the hydrogen content per unit volume of said calibration layer and of said sample, using a nuclear magnetic resonance sensor.

9. The method of claim 5, wherein said physical characteristic is a dielectric property, and wherein said sensing steps are performed by sensing the dielectric property of said calibration layer and of said sample.

10. The method of claim 5, wherein said selecting step is performed by determining a range of expected values of said physical characteristic of said product, and selecting said calibration layer such that said reference value is within said range.

11. The method of claim 5, further comprising the step of converting said signal to digital values, and wherein said comparing, determining, and adjusting steps are performed with digital processing means.

12. The method of claim 5, wherein said comparing, determining, and adjusting steps are performed with analog processing means.

13. A method of calibrating a sampler that measures a physical property of a product in a container, comprising the steps of:

selecting a calibration material having physical characteristics that provide an expected sensor output;

placing a sampling tube under an aperture at the bottom of said container, at least part of said sampling tube being within the sensory area of a sensor;

moving a piston inside said sampling tube, said piston having at least a layer made from said calibration material, to a position such that said layer is within the sensory area of said sensor, wherein said layer forms an integral body with the rest of said piston and whereby no piston structure is positioned between the side surface of the layer and sampling tube;

sensing said layer, thereby obtaining a signal representing a measured sensor output of said layer;

comparing the measured sensor output of said layer to said expected sensor value; and adjusting the output of said sensor, based on the results of said comparing step.

14. The method of claim 13, wherein said expected sensor output is zero and said adjusting step is performed by adjusting the zero point of said sensor.

15. The method of claim 13, wherein said adjusting step is performed by determining a calibration factor.

16. A sampling and measuring system for obtaining a sample of a product from a container having a sampling aperture, and for measuring a physical property of the sample, comprising:

a sampling device having a sampling tube for attachment to said container, such that it receives said sample via said sampling aperture, said sampling tube having a port end in communication with said sampling aperture and having a stopper end opposite said port end; a piston moveable within said sampling tube, having a substantially sealed relationship with the inner walls of said sampling tube such that said piston may be moved upwardly within said sampling tube to provide an upward force at the bottom surface of said sample to return said sample to said container via said sampling aperture, said piston having at least a layer of calibrating material that is an integral part of said piston; and a sensor for sensing said physical characteristic of said sample while said sample is within said sample tube; wherein said layer has at least one physical characteristic that provides a known expected output of said sensor and whereby no piston structure is positioned between the side surface of the layer and sampling tube;

a calibration mode selector for initiating a calibration mode of said sampler;

a piston control processor in communication with said calibration mode selector, for placing said piston in a calibration position, such that said calibration layer is within the sensory area of said sensor; and a calibrator in communication with said calibration mode selector, for receiving a measured signal from said sensor while said piston is in said calibration position and for comparing said measured signal with a reference signal.

17. The apparatus of claim 1, wherein said calibrating material provides an expected sensor output of zero.

18. The apparatus of claim 1, wherein said calibrating material has a physical characteristic similar to said physical characteristic measured by said sensor.

19. The system of claim 16, wherein said piston is entirely made from said calibrating material.

* * * * *